US010632132B2

United States Patent
Batthyány et al.

(10) Patent No.: US 10,632,132 B2
(45) Date of Patent: Apr. 28, 2020

(54) METHODS FOR TREATING HEART TRANSPLANT REJECTION

(71) Applicants: Carlos Batthyány, Montevideo (UY); Gloria Virginia López, Montevideo (UY); Carlos Escande, Montevideo (UY); Williams Arturo Porcal Quinta, Montevideo (UY); Germán Adrian Galliussi López, Montevideo (UY); Marcelo Hill, Canelones (UY); Mercedes Segovia, Canelones (UY)

(72) Inventors: Carlos Batthyány, Montevideo (UY); Gloria Virginia López, Montevideo (UY); Carlos Escande, Montevideo (UY); Williams Arturo Porcal Quinta, Montevideo (UY); Germán Adrian Galliussi López, Montevideo (UY); Marcelo Hill, Canelones (UY); Mercedes Segovia, Canelones (UY)

(*) Notice: Subject to any disclaimer, the term of this patent is extended or adjusted under 35 U.S.C. 154(b) by 0 days.

(21) Appl. No.: 16/256,235

(22) Filed: Jan. 24, 2019

(65) Prior Publication Data
US 2019/0255077 A1    Aug. 22, 2019

Related U.S. Application Data

(60) Provisional application No. 62/621,228, filed on Jan. 24, 2018.

(51) Int. Cl.
| | |
|---|---|
| *A61K 31/60* | (2006.01) |
| *A61P 37/06* | (2006.01) |
| *A61P 29/00* | (2006.01) |
| *A61K 31/192* | (2006.01) |
| *A61K 45/06* | (2006.01) |

(52) U.S. Cl.
CPC ............ *A61K 31/60* (2013.01); *A61K 31/192* (2013.01); *A61P 29/00* (2018.01); *A61P 37/06* (2018.01); *A61K 45/06* (2013.01)

(58) Field of Classification Search
None
See application file for complete search history.

(56) References Cited

PUBLICATIONS

Shaw. Comparison of the effects of acetylsalicylic acid and sodium salicylate on prolongation of rat cardiac allograft survival and on inhibition of rat platelet aggregation. Transplantation, vol. 36, No. 1, 1983.*

* cited by examiner

*Primary Examiner* — Anna Pagonakis
(74) *Attorney, Agent, or Firm* — Cozen O'Connor

(57) ABSTRACT

Current therapeutic approach to treating heart allotransplantation rejection focus on immunosuppression protocols that carry harmful side effects after chronic use, which include global immune depression to the patient. The present inventors have discovered alternative and synergistic protocols based on inhibiting NF-κB and NLRP3 inflammasome-dependent IL-1β release with nitrated NSAID derivatives.

6 Claims, 3 Drawing Sheets

METHODS FOR TREATING HEART TRANSPLANT REJECTION

CROSS REFERENCE TO RELATED APPLICATIONS

This application claims the benefit of U.S. Provisional Application 62/621,228 filed Jan. 24, 2018

BACKGROUND

Heart transplantation is currently the only definitive solution when a heart has total failure of its functions. In clinical practice allografts of the heart are usually performed, necessarily carrying immunosuppression protocols to avoid acute rejection. However, chronic rejection has not yet been successfully managed. In addition, the side effects associated with the chronic use of immunosupressants constitute a therapeutic problem due to their toxicity and the fact that they generate a global immunodepression to the patient. Currently, therapeutic strategies are sought to avoid their chronic use and high doses of them. Until now, all therapies to avoid the rejection of allotransplantation had as objective the manipulation of the adaptive immunity. Thus, there is a need to develop a novel therapeutic protocol, which includes a combination with classical immunosuppressants (administered in low doses and short duration) in order to obtain synergistic and long-term effects for allograft survival.

SUMMARY

One embodiment of the described invention is a therapeutic approach to treat heart allotransplantation rejection based on the inflammasome inhibition with a new anti-inflammatory nitroalkene.

One embodiment is a method of treating heart transplant rejection comprising administering to a subject in need thereof an effective amount of a compound of Formula I:

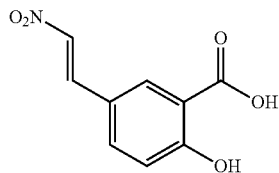

Another embodiment includes a method of treating heart transplant rejection comprising administering to a subject in need thereof an effective amount of a compound of Formula I:

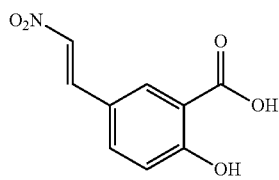

further comprising administering one or more secondary therapeutic agents.

Another embodiment includes a method of treating heart transplant rejection comprising administering to a subject in need thereof an effective amount of a compound of Formula I:

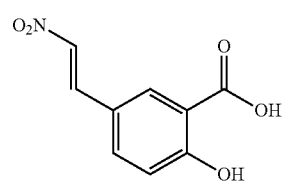

further comprising administering one or more secondary therapeutic agents, wherein the one or more secondary therapeutic agents is selected from the group consisting of calcineurin inhibitors, corticosteroids, cytotoxic immunosuppressants, immunosuppressant antibodies, sirolimus derivatives, other immunosuppressants, and any combination thereof.

One embodiment is method of treating heart transplant rejection in a subject comprising administering to said subject a pharmaceutical composition comprised of an effective amount of a compound of Formula I:

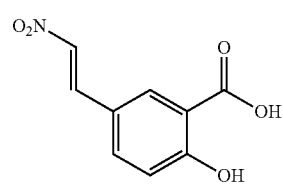

or a pharmaceutically acceptable salt thereof, and a carrier.

Another embodiment includes a method of treating heart transplant rejection in a subject comprising administering to said subject a pharmaceutical composition comprised of an effective amount of a compound of Formula I:

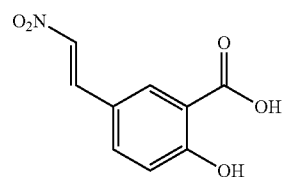

or a pharmaceutically acceptable salt thereof, and a carrier, wherein the pharmaceutical composition further comprises one or more secondary therapeutic agents.

Another embodiment includes a method of treating heart transplant rejection in a subject comprising administering to said subject a pharmaceutical composition comprised of an effective amount of a compound of Formula I:

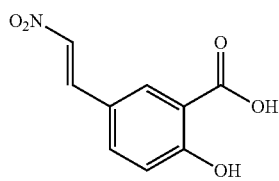

or a pharmaceutically acceptable salt thereof, and a carrier, wherein the pharmaceutical composition further comprises one or more secondary therapeutic agents selected from the group consisting of calcineurin inhibitors, corticosteroids, cytotoxic immunosuppressants, immunosuppressant antibodies, sirolimus derivatives, other immunosuppressants, and any combination thereof.

DESCRIPTION

Figure 1:
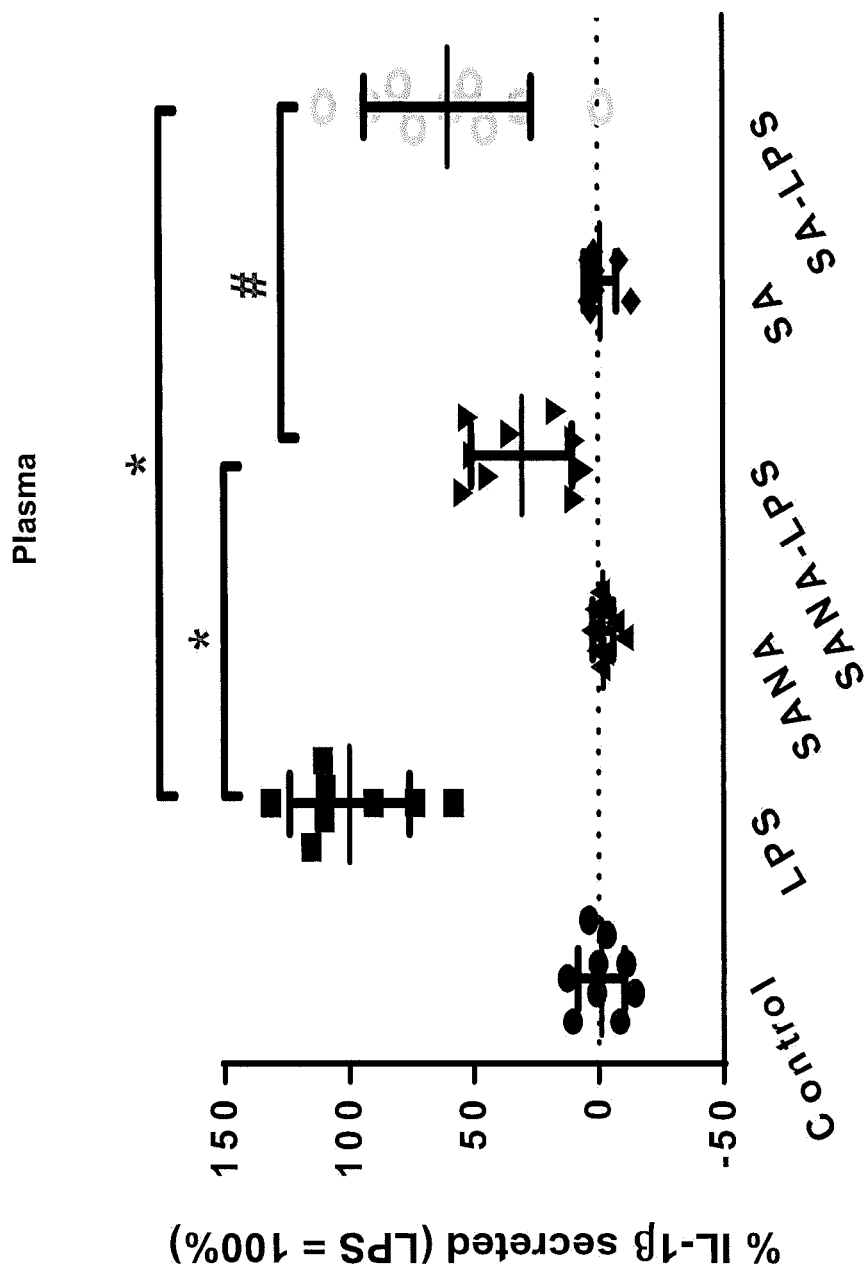
FIG. 1 demonstrates the inhibitory effect of SANA on NF-κB and NLRP3 inflamasome-dependent IL-1β release in the plasma of C57BL/6 mice.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a," "an," and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 5% of the numerical value of the number with which it is being used. Therefore, about 50% means in the range of 45%-55%.

"Administering" when used in conjunction with a therapeutic means to administer a therapeutic directly to a subject, whereby the agent positively impacts the target. "Administering" a composition may be accomplished by, for example, injection, oral administration, topical administration, or by these methods in combination with other known techniques. Such combination techniques include heating, radiation, ultrasound and the use of delivery agents. When a compound is provided in combination with one or more other active agents, "administration" and its variants are each understood to include concurrent and sequential provision of the compound or salt and other agents.

By "pharmaceutically acceptable" it is meant the carrier, diluent, adjuvant, or excipient must be compatible with the other ingredients of the formulation and not deleterious to the recipient thereof.

"Composition" as used herein is intended to encompass a product comprising the specified ingredients in the specified amounts, as well as any product which results, directly or indirectly, from combination of the specified ingredients in the specified amounts. Such term in relation to "pharmaceutical composition" is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

As used herein, the term "agent," "active agent," "therapeutic agent," or "therapeutic" means a compound or composition utilized to treat, combat, ameliorate, prevent or improve an unwanted condition or disease of a patient. Furthermore, the term "agent," "active agent," "therapeutic agent," or "therapeutic" encompasses a combination of one or more of the compounds of the present invention.

A "therapeutically effective amount" or "effective amount" of a composition is a predetermined amount calculated to achieve the desired effect, i.e., to inhibit, block, or reverse the activation, migration, proliferation, alteration of cellular function, and to preserve the normal function of cells. The activity contemplated by the methods described herein includes both medical therapeutic and/or prophylactic treatment, as appropriate, and the compositions of the invention may be used to provide improvement in any of the conditions described. It is also contemplated that the compositions described herein may be administered to healthy subjects or individuals not exhibiting symptoms but who may be at risk of developing a particular disorder. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the chosen dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," or "treating" as used herein refer to both therapeutic treatment and prophylactic or preventative measures, wherein the object is to prevent or slow down (lessen) an undesired physiological condition, disorder, or disease, or to obtain beneficial or desired clinical results. For the purposes of this invention, beneficial or desired results include, but are not limited to, alleviation of symptoms; diminishment of the extent of the condition, disorder, or disease; stabilization (i.e., not worsening) of the state of the condition, disorder, or disease; delay in onset or slowing of the progression of the condition, disorder, or disease; amelioration of the condition, disorder, or disease state; and remission (whether partial or total), whether detectable or undetectable, or enhancement or improvement of the condition, disorder, or disease. Treatment includes prolonging survival as compared to expected survival if not receiving treatment.

The term "subject," as used herein, describes an organism, including mammals, to which treatment with the compositions and compounds according to the subject disclosure can be administered. Mammalian species that can benefit from the disclosed methods include, but are not limited to, apes, chimpanzees, orangutans, humans, monkeys; and other animals such as dogs, cats, horses, cattle, pigs, sheep, goats, chickens, mice, rats, guinea pigs, and hamsters. Typically, the subject is a human.

The term "tissue," as used herein, describes an aggregate of cells typically of a particular kind together with their intercellular substance that form one of the structural materials of a subject. The term "organ," as used herein, describes a group of tissues that perform a specific function. For example, heart is a type of organ embodied herein.

Administration and Compositions

The compounds and pharmaceutically-acceptable salts thereof can be administered by means that produces contact of the active agent with the agent's site of action. They can be administered by conventional means available for use in conjunction with pharmaceuticals in a dosage range of 0.001 to 1000 mg/kg of mammal (e.g. human) body weight per day in a single dose or in divided doses. One dosage range is 0.01 to 500 mg/kg body weight per day orally in a single dose or in divided doses. Administration can be delivered as individual therapeutic agents or in a combination of therapeutic agents. They can be administered alone, but typically are administered with a pharmaceutically acceptable excipient selected on the basis of the chosen route of administration and standard pharmaceutical practice.

Compounds can be administered by one or more ways. For example, the following routes may be utilized: oral, parenteral (including subcutaneous injections, intravenous, intramuscular, intrasternal injection or infusion techniques), inhalation, buccal, sublingual, or rectal, in the form of a unit dosage of a pharmaceutical composition containing an effective amount of the compound and optionally in combination with one or more pharmaceutically-acceptable excipients such as stabilizers, anti-oxidants, lubricants, bulking agents, fillers, carriers, adjuvants, vehicles, diluents and other readily known excipients in standard pharmaceutical practice.

Liquid preparations suitable for oral administration (e.g. suspensions, syrups, elixirs and other similar liquids) can employ media such as water, glycols, oils, alcohols, and the like. Solid preparations suitable for oral administration (e.g. powders, pills, capsules and tablets) can employ solid excipients such as starches, sugars, kaolin, lubricants, binders, disintegrating agents, antioxidants and the like.

Parenteral compositions typically employ sterile water as a carrier and optionally other ingredients, such as solubility aids. Injectable solutions can be prepared, for example, using a carrier comprising a saline solution, a glucose solution or a solution containing a mixture of saline and glucose. Further guidance for methods suitable for use in preparing pharmaceutical compositions is provided in *Remington: The Science and Practice of Pharmacy*, 21$^{st}$ edition (Lippincott Williams & Wilkins, 2006).

Therapeutic compounds can be administered orally in a dosage range of about 0.001 to 1000 mg/kg of mammal (e.g. human) body weight per day in a single dose or in divided doses. One dosage range is about 0.01 to 500 mg/kg body weight per day orally in a single dose or in divided doses. For oral administration, the compositions can be provided in the form of tablets or capsules containing about 1.0 to 500 mg of the active ingredient, particularly about 1, 5, 10, 15, 20, 25, 50, 75, 100, 150, 200, 250, 300, 400, 500, and 750 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the subject undergoing therapy. In view of the factors affecting the specific dose level and frequency it is contemplated that the dose frequency can range from multiple doses daily to monthly dosages. The preferred dose frequency ranges from twice a day to every two weeks. A more preferred dose frequency ranges from twice a day to weekly. A most preferred dose frequency ranges from twice a day to twice a week.

In the methods of various embodiments, pharmaceutical compositions including the active agent can be administered to a subject in an "effective amount." An effective amount may be any amount that provides a beneficial effect to the patient, and in particular embodiments, the effective amount is an amount that may: (1) prevent or reduce rejection of heart tissue allografts and (2) prevent or reduce rejection of a transplanted heart.

Pharmaceutical formulations containing the compounds of the invention and a suitable carrier can be in various forms including, but not limited to, solids, solutions, powders, fluid emulsions, fluid suspensions, semi-solids, and dry powders including an effective amount of an the active agent of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, antioxidants, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's, The Pharmaceutical Basis of Therapeutics*, 6th Edition, MacMillan Publishing Co., New York (1980) both of which are hereby incorporated by reference in their entireties can be consulted.

Other embodiments of the invention include the active agent prepared as described above which are formulated as a solid dosage form for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings.

In another exemplary embodiment, an oily preparation of an active agent prepared as described above may be lyophilized to form a solid that may be mixed with one or more pharmaceutically acceptable excipient, carrier or diluent to form a tablet, and in yet another embodiment, the active agent may be crystallized to from a solid which may be combined with a pharmaceutically acceptable excipient, carrier or diluent to form a tablet.

The means and methods for tableting are known in the art and one of ordinary skill in the art can refer to various references for guidance. For example, *Pharmaceutical Manufacturing Handbook: Production and Processes*, Shayne Cox Gad, John Wiley & Sons, Inc., Hoboken, N.J. (2008), which is hereby incorporated by reference in its entirety can be consulted.

Further embodiments which may be useful for oral administration of the active agent include liquid dosage forms. In such embodiments, a liquid dosage may include a pharmaceutically acceptable emulsion, solution, suspension, syrup, and elixir containing inert diluents commonly used in the art, such as water. Such compositions may also comprise adjuvants, such as wetting agents, emulsifying and suspending agents, and sweetening, flavoring, and perfuming agents. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt. Other suitable diluents include, but are not limited to those described below:

Vegetable oil: As used herein, the term "vegetable oil" refers to a compound, or mixture of compounds, formed from ethoxylation of vegetable oil, wherein at least one chain of polyethylene glycol is covalently bound to the vegetable oil. In some embodiments, the fatty acids may have between about twelve carbons to about eighteen carbons. In some embodiments, the amount of ethoxylation can vary from about 2 to about 200, about 5 to 100, about 10 to about 80, about 20 to about 60, or about 12 to about 18 of ethylene glycol repeat units. The vegetable oil may be hydrogenated or unhydrogenated. Suitable vegetable oils include, but are not limited to castor oil, hydrogenated castor oil, sesame oil, corn oil, peanut oil, olive oil, sunflower oil, safflower oil, soybean oil, benzyl benzoate, sesame oil, cottonseed oil, and palm oil. Other suitable vegetable oils include commercially available synthetic oils such as, but not limited to, Miglyol™ 810 and 812 (available from Dynamit Nobel Chemicals, Sweden) Neobee™ M5 (available from Drew Chemical Corp.), Alofine™ (available from Jarchem Industries), the Lubritab™ series (available from JRS Pharma), the Sterotex™ (available from Abitec Corp.), Softisan™ 154 (available from Sasol), Croduret™ (available from Croda), Fancol™ (available from the Fanning Corp.), Cutina™ HR (available from Cognis), Simulsol™ (available from CJ Petrow), EmCon™ CO (available from Amisol Co.), Lipvol™ CO, SES, and HS-K (available from Lipo), and Sterotex™ HM (available from Abitec Corp.). Other suitable vegetable oils, including sesame, castor, corn, and cottonseed oils, include those listed in R. C. Rowe and P. J. Shesky, *Handbook of Pharmaceutical Excipients*, (2006), 5th ed., which is incorporated herein by reference in its entirety. Suitable polyethoxylated vegetable oils, include but are not limited to, Cremaphor™ EL or RH series (available from BASF), Emulphor™ EL-719 (available from Stepan products), and Emulphor™ EL-620P (available from GAF).

Mineral oils: As used herein, the term "mineral oil" refers to both unrefined and refined (light) mineral oil. Suitable mineral oils include, but are not limited to, the Avatech™ grades (available from Avatar Corp.), Drakeol™ grades (available from Penreco), Sirius™ grades (available from Shell), and the Citation™ grades (available from Avater Corp.).

Castor oils: As used herein, the term "castor oil," refers to a compound formed from the ethoxylation of castor oil, wherein at least one chain of polyethylene glycol is covalently bound to the castor oil. The castor oil may be hydrogenated or unhydrogenated. Synonyms for polyethoxylated castor oil include, but are not limited to polyoxyl castor oil, hydrogenated polyoxyl castor oil, mcrogolglyceroli ricinoleas, macrogolglyceroli hydroxystearas, polyoxyl 35 castor oil, and polyoxyl 40 hydrogenated castor oil. Suitable polyethoxylated castor oils include, but are not limited to, the Nikkol™ HCO series (available from Nikko Chemicals Co. Ltd.), such as Nikkol HCO-30, HC-40, HC-50, and HC-60 (polyethylene glycol-30 hydrogenated castor oil, polyethylene glycol-40 hydrogenated castor oil, polyethylene glycol-50 hydrogenated castor oil, and polyethylene glycol-60 hydrogenated castor oil, Emulphor™ EL-719 (castor oil 40 mole-ethoxylate, available from Stepan Products), the Cremophore™ series (available from BASF), which includes Cremophore RH40, RH60, and EL35 (polyethylene glycol-40 hydrogenated castor oil, polyethylene glycol-60 hydrogenated castor oil, and polyethylene glycol-35 hydrogenated castor oil, respectively), and the Emulgin® RO and HRE series (available from Cognis PharmaLine). Other suitable polyoxyethylene castor oil derivatives include those listed in R. C. Rowe and P. J. Shesky, *Handbook of Pharmaceutical Excipients*, (2006), 5th ed., which is incorporated herein by reference in its entirety.

Sterol: As used herein, the term "sterol" refers to a compound, or mixture of compounds, derived from the ethoxylation of sterol molecule. Suitable polyethoyxlated sterols include, but are not limited to, PEG-24 cholesterol ether, Solulan™ C-24 (available from Amerchol); PEG-30 cholestanol, Nikkol™ DHC (available from Nikko); Phytosterol, GENEROL™ series (available from Henkel); PEG-25 phyto sterol, Nikkol™ BPSH-25 (available from Nikko); PEG-5 soya sterol, Nikkol™ BPS-5 (available from Nikko); PEG-10 soya sterol, Nikkol™ BPS-10 (available from Nikko); PEG-20 soya sterol, Nikkol™ BPS-20 (available from Nikko); and PEG-30 soya sterol, Nikkol™ BPS-30 (available from Nikko).

Polyethylene glycol: As used herein, the term "polyethylene glycol" or "PEG" refers to a polymer containing ethylene glycol monomer units of formula —O—CH$_2$—CH$_2$—. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer. In some embodiments, the polyethylene glycol is polyethylene glycol-400. Suitable polyethylene glycols include, but are not limited to the Carbowax™ and Carbowax™ Sentry series (available from Dow), the Lipoxol™ series (available from Brenntag), the Lutrol™ series (available from BASF), and the Pluriol™ series (available from BASF).

Propylene glycol fatty acid ester: As used herein, the term "propylene glycol fatty acid ester" refers to a monoether or diester, or mixtures thereof, formed between propylene glycol or polypropylene glycol and a fatty acid. Fatty acids that are useful for deriving propylene glycol fatty alcohol ethers include, but are not limited to, those defined herein. In some embodiments, the monoester or diester is derived from propylene glycol. In some embodiments, the monoester or diester has about 1 to about 200 oxypropylene units. In some embodiments, the polypropylene glycol portion of the molecule has about 2 to about 100 oxypropylene units. In some embodiments, the monoester or diester has about 4 to about 50 oxypropylene units. In some embodiments, the monoester or diester has about 4 to about 30 oxypropylene units. Suitable propylene glycol fatty acid esters include, but are not limited to, propylene glycol laurates: Lauroglycol™ FCC and 90 (available from Gattefosse); propylene glycol caprylates: Capryol™ PGMC and 90 (available from Gatefosse); and propylene glycol dicaprylocaprates: Labrafac™ PG (available from Gatefosse).

Stearoyl macrogol glyceride: Stearoyl macrogol glyceride refers to a polyglycolized glyceride synthesized predominately from stearic acid or from compounds derived predominately from stearic acid, although other fatty acids or compounds derived from other fatty acids may be used in the synthesis as well. Suitable stearoyl macrogol glycerides include, but are not limited to, Gelucire® 50/13 (available from Gattefossé).

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

Exemplary excipients or carriers for use in solid and/or liquid dosage forms include, but are not limited to:

Sorbitol: Suitable sorbitols include, but are not limited to, PharmSorbidex E420 (available from Cargill), Liponic 70-NC and 76-NC (available from Lipo Chemical), Neosorb (available from Roquette), Partech SI (available from Merck), and Sorbogem (available from SPI Polyols).

Starch, sodium starch glycolate, and pregelatinized starch include, but are not limited to, those described in R. C. Rowe and P. J. Shesky, *Handbook of Pharmaceutical Excipients*, (2006), 5th ed., which is incorporated herein by reference in its entirety.

Disintegrant: The disintegrant may include one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

Still further embodiments of the invention include the active agent administered in combination with other active such as, for example, adjuvants, or other compatible drugs or compounds where such combination is seen to be desirable or advantageous in achieving the desired effects of the methods described herein.

Other embodiments of the present invention include a pharmaceutical composition comprising an effective amount of the active agent and one or more pharmaceutically acceptable excipient. Other embodiments include a pharmaceutical composition comprising an effective amount of pharmaceutically-acceptable salts of the active agent. Other embodiments include a pharmaceutical composition comprising an effective amount of pharmaceutically-acceptable salts of active agent and a pharmaceutically-acceptable excipient.

In yet other embodiments, the active agent may be administered simultaneously or separately with one or more secondary therapeutic agents. Secondary therapeutic agents may include but are not limited to: immunosuppressant agents such as calcineurin inhibitors (cyclosporin, tacrolimus), corticosteroids (methylprednisolone, dexamethasone, prednisolone), cytotoxic immunosuppressants (azathioprine, chlorambucil, cyclophosphamide, mercaptopurine, methotrexate), immunosuppressant antibodies (eg antithymocyte globulins, basiliximab, infliximab), sirolimus derivatives (everolimus, sirolimus), other immunosuppressants (mycophenolate), and any combination thereof.

The compound of Formula I and pharmaceutical compositions thereof as described herein may be administered to subjects to treat tissue allograft rejection. In other embodiments, the compound of Formula I and pharmaceutical compositions thereof as described herein may be administered to subjects to prevent or reduce rejection of a transplanted organ. In some embodiments the compound of Formula I and pharmaceutical compositions thereof as described herein may be administered to subjects to prevent or reduce rejection of a transplanted heart. In some embodiments, the compound of Formula I and pharmaceutical compositions thereof as described herein may be used to prolong the survival of a transplanted heart.

EXAMPLES

The following examples contain detailed methods of preparing compounds of Formula I. These detailed descriptions serve to exemplify the above general synthetic schemes which form part of the invention. These detailed descriptions are presented for illustrative purposes only and are not intended as a restriction on the scope of the invention. All parts are by weight and temperatures are in Degrees Celsius unless otherwise indicated. All compounds showed NMR spectra consistent with their assigned structures.

Example 1: 2-hydroxy-5-(2-nitroethenyl)benzoic acid (SANA)

To a solution of 5-formylsalicylic (1 g, 6.02 mmol) in ethanol (16.5 mL), nitromethane (5.5 mL, 0.10 mmol) and ammonium acetate (1.39 g, 18.06 mmol) were added. The reaction mixture is heated at 60° C. for 1 h, allowed to cool to room temperature and put in refrigerator for 15 minutes. Formed orange precipitate was filtered off and dissolved in water (ca. 250 mL). Solution was acidified with concentrated HCl (ca. 10 drops) until total precipitation. Formed yellow solid was filtered off and dried in vacuo. Yield: 1.18 g (93%).

1H NMR (acetone-$d_6$): δ=8.35 (d, J=2.3 Hz, 1H), 8.14 (d, J=13.7, 1H), 8.06 (dd, J=8.7 2.3 Hz, 1H), 7.99 (d, J=13.7 Hz, 1H), 7.11 (d, J=8.7 Hz, 1H). 13C NMR (acetone-d6): δ=171.09, 164.66, 137.94, 136.51, 135.94, 133.21, 121.95, 118.51, 113.08

Biologic Activity

The following methods described are used in order to demonstrate biological activity and therapeutic use, and should not to be construed in any way as limiting the scope of the invention.

Figure 2:
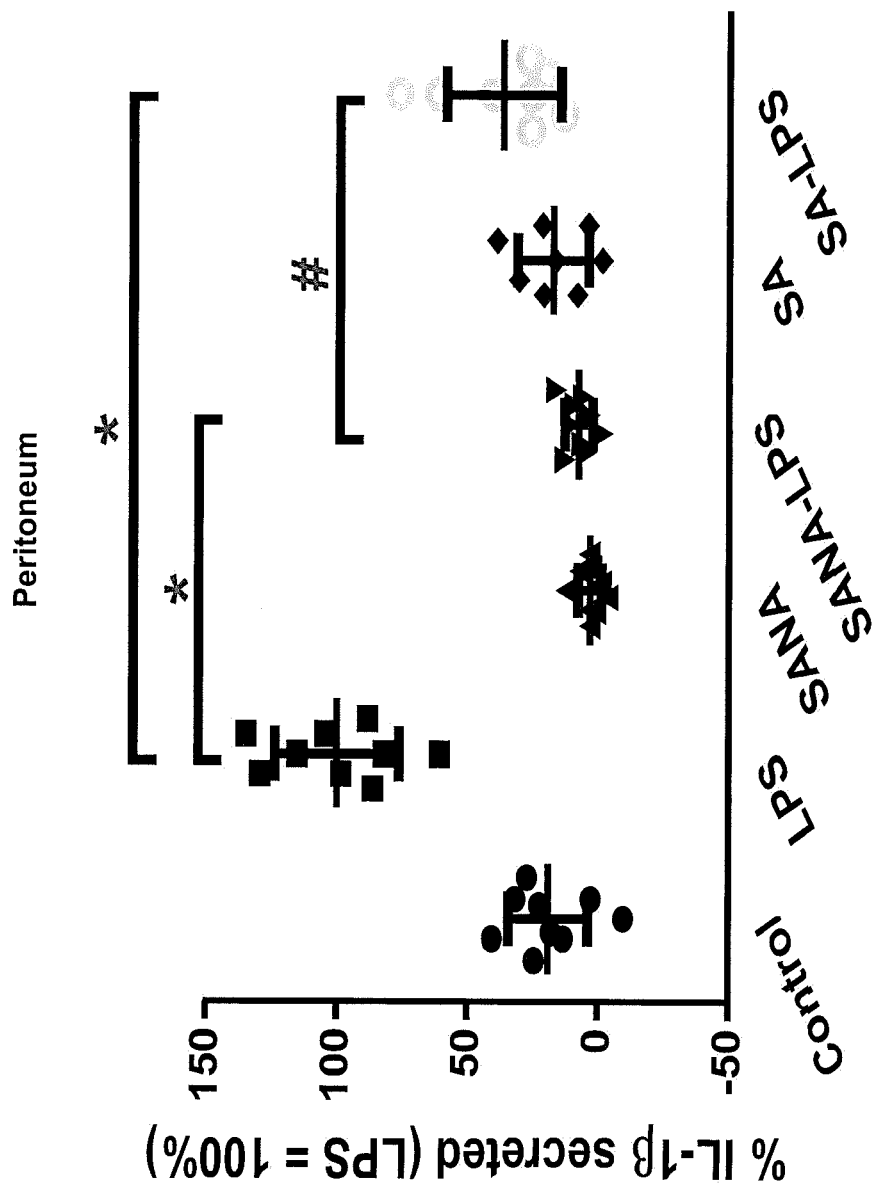
FIG. 2 demonstrates the inhibitory effect of SANA on NF-κB and NLRP3 inflamasome-dependent IL-1β release in the peritoneum of C57BL/6 mice.
Figure 3:
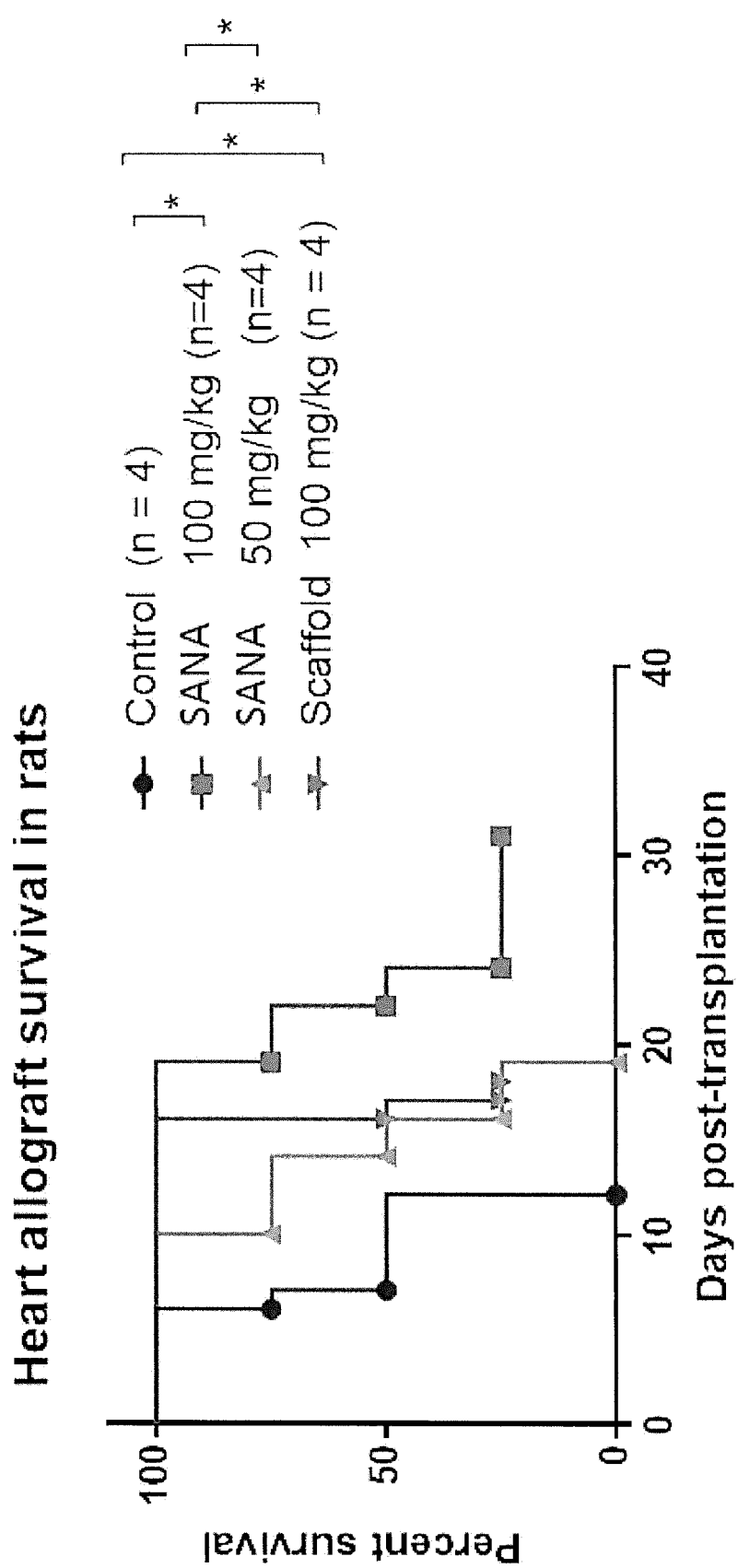
FIG. 3 demonstrates prolonged survival for fully mismatched heterotopic heart allograft in rat models treated with SANA.

While not wishing to be bound by theory, NLRP3 inflammasome activation is a mechanism that mediates the rejection of allotransplantation and in one embodiment of the described invention, it is a possible therapeutic target to treat allotransplantation of a heart. As shown in FIGS. 1 and 2, SANA, in vivo, inhibits NF-κB and the NLRP3 inflammasome-dependent IL-1β release. C57BL/6 mice were treated with SANA or salicylic acid (SA) (100 mg/kg, IP) or the vehicle (DMSO) for 1 hour. Then were injected with LPS (10 mg/kg, IP) or PBS for 2 hours, with subsequent peritoneal washes and blood extractions. Peritoneal wash and plasma were stored to measure IL-1β by ELISA. FIG. 3 demonstrated SANA in a rat model, for a fully mismatched heterotopic heart allograft, prolonged the heart grafted survival respect to the control and its precursor drug. Rats were administrated with SANA or SA (100 mg/kg), SANA (50 mg/kg) or vehicle (Phosphate buffer) by oral gavage every day since day −1 until day 15 post-transplantation. Heart heterotopic transplantation was done by implantation of the donor heart (Lewis 1W rat) into the receptor abdomen (Lewis 1A rat). Rejection was diagnosed when the heart lost functionality (beats has stopped).

What is claimed is:

1. A method of treating heart transplant rejection comprising administering to a subject in need thereof an effective amount of a compound of Formula I:

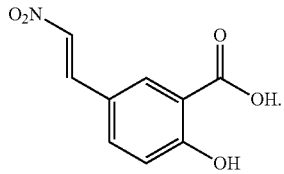 [SMILES: O=C(O)c1cc(/C=C/[N+](=O)[O-])ccc1O]

2. The method of claim 1, further comprising administering one or more secondary therapeutic agents.

3. The method of claim 2, wherein the one or more secondary therapeutic agents is selected from the group consisting of calcineurin inhibitors, cytotoxic immunosuppressants, and immunosuppressant antibodies, and any combination thereof.

4. A method of treating heart transplant rejection in a subject comprising administering to said subject a pharmaceutical composition comprised of an effective amount of a compound of Formula I:

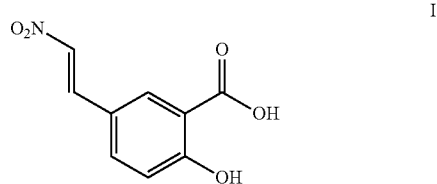 [SMILES: O=C(O)c1cc(/C=C/[N+](=O)[O-])ccc1O]

or a pharmaceutically acceptable salt thereof, and a carrier.

5. The method of claim 4, wherein the pharmaceutical composition further comprises one or more secondary therapeutic agents.

6. The method of claim 5, wherein the one or more secondary therapeutic agents is selected from the group consisting of calcineurin inhibitors, cytotoxic immunosuppressants, and immunosuppressant antibodies, and any combination thereof.

* * * * *